(12) United States Patent
Bi

(10) Patent No.: US 11,378,568 B1
(45) Date of Patent: Jul. 5, 2022

(54) CEMENT ANALYZER MEASURES GAS MIGRATION AND COMPRESSIVE STRENGTH

(71) Applicant: Hongfeng Bi, Houston, TX (US)

(72) Inventor: Hongfeng Bi, Houston, TX (US)

(73) Assignee: HONGFENG BI, Houston, TX (US)

(*) Notice: Subject to any disclaimer, the term of this patent is extended or adjusted under 35 U.S.C. 154(b) by 0 days.

(21) Appl. No.: 16/865,381

(22) Filed: May 3, 2020

(51) Int. Cl.
*G01N 33/38* (2006.01)
*G01N 29/024* (2006.01)
*G01F 1/00* (2022.01)
*H05B 1/02* (2006.01)
*G01L 13/00* (2006.01)

(52) U.S. Cl.
CPC .......... *G01N 33/383* (2013.01); *G01F 1/00* (2013.01); *G01L 13/00* (2013.01); *G01N 29/024* (2013.01); *H05B 1/0288* (2013.01); *G01N 2291/011* (2013.01)

(58) Field of Classification Search
CPC .............. G01N 33/383; G01N 29/024; G01N 2291/011; G01F 1/00; G01L 13/00; H05B 1/0288
See application file for complete search history.

(56) References Cited

U.S. PATENT DOCUMENTS

| 4,259,868 | A | 4/1981 | Rao et al. | |
|---|---|---|---|---|
| 4,648,264 | A | 3/1987 | Freese et al. | |
| 6,269,684 | B1* | 8/2001 | Maki, Jr. ............... | E21B 49/005 73/53.01 |
| 8,418,526 | B2 | 4/2013 | He et al. | |
| 9,612,187 | B1 | 4/2017 | Sun et al. | |
| 2004/0199340 | A1* | 10/2004 | Kersey ................. | G01N 29/024 702/50 |
| 2011/0107848 | A1* | 5/2011 | Le Roy-Delage ... | G01N 33/383 73/861.42 |
| 2012/0118041 | A1* | 5/2012 | He .......................... | G01N 7/14 73/23.35 |
| 2019/0111395 | A1* | 4/2019 | Greenizen ............... | B25B 5/16 |
| 2020/0240955 | A1* | 7/2020 | Jandhyala ............ | E21B 47/005 |
| 2020/0340973 | A1* | 10/2020 | Hakimuddin ........ | G01N 29/024 |

* cited by examiner

*Primary Examiner* — Randy W Gibson
*Assistant Examiner* — John M Royston

(57) ABSTRACT

The present invention pertains to a method and experimental apparatus for studying properties of cement slurry to be used in an oil or gas well under varied pressure and temperature conditions. This apparatus can be used to predict the likelihood of gas migration, compressive strength and static gel strength of cement slurry. It comprises a servo motor and coupling magnets to drive a paddle at a very slow speed through the cement in a pressure vessel, a pair of acoustic transducers to generate an acoustic signal and measure the transit time of the acoustic signal after it transits the cement, and a gas injection system to predict the severity of gas migration in cement.

6 Claims, 2 Drawing Sheets

CEMENT ANALYZER MEASURES GAS MIGRATION AND COMPRESSIVE STRENGTH

CROSS-REFERENCE TO RELATED APPLICATIONS

This is a division of application Ser. No. 15/875,621, filed Jan. 19, 2018.

BACKGROUND

Field of Invention

The present invention pertains to a method and experimental apparatus for studying properties of cement slurry to be used in oil or gas well under varied pressure and temperature conditions. This apparatus can be used to predict the likelihood of gas migration, determine compressive strength as well as static gel strength of cement slurry. The cement analyzer comprises a servo motor and coupling magnets to drive a paddle at a very slow speed through the cement in a pressure vessel, a pair of acoustic transducers to generate an acoustic signal and record the transit time of the acoustic signal after it transits the cement, and a gas injection system to evaluate the potential and severity of gas migration of cement sample.

Description of Prior Art

Cementing is a process of mixing slurry of cement and water and pumping it down to the annulus space around casing. The two principal functions of cementing are to restrict fluid movement between formation and open hole and to bond and support the casing. Gas migration is the invasion of formation fluids (gas in this case) into the annulus due to a pressure imbalance at the formation, where the fluids (gas) may migrate to a lower pressure zone or possibly to the surface. Gas migration through the cement slurry and into the wellbore from a gas bearing formation has the potential to cause significant problems for well operators. Therefore, it is imperative to know and understand the properties of this fluid and to determine how these properties are affected by different formation conditions.

U.S. Pat. No. 4,259,868 introduces a method and apparatus for the nondestructive testing of cement slurry samples as a function of time. A sample placed in a temperature and pressure controlled autoclave is coupled to transducer means under computer control. Ultrasonic energy is propagated through sample and the transit time is measured and developed to compressive strength. However, this system can't be used to analyze the severity of gas migration of cement.

U.S. Pat. No. 4,648,264 introduces a transportable apparatus that can measure compressibility, thickening time and static gel strength of a sample of slurry by a single container. A load cell is directly connected to a drive mechanism for driving a paddle at very slow speed through the sample. However, this apparatus can't be used to analyze severity of gas migration of cement.

U.S. Pat. No. 8,418,526 presents a method and system for testing gas migration process in the coal and rock mass. It comprises step of selecting a cylindrical coal sample, applying axial pressure, radial pressure control and temperature control, for absorbing the gas absorbed in the coal sample, and guiding the gas desorbed from the coal sample via a guiding passage, detecting flow rate and pressure of the gas, as well as analyzing composition and content of the gas. However, this system can't be used to measure cement static gel strength and compressive strength.

U.S. Pat. No. 9,612,187 brings an apparatus for studying the gas invasion and migration mechanism in oil and gas wellbore, which can be used to study the mechanism of strata gas invasion into wellbores and the mechanism of gas bubble migration, merging or phase transition in wellbores, in order to provide an experimental basis for establishing a theoretical model of gas kick and theoretical support for the safe and efficient offshore deep water well drilling. However, this system can't be used to measure static gel strength and compressive strength.

It is an object of this invention to provide a practical and affordable method for accurately predicting the likelihood of gas migration, determine compressive strength as well as static gel strength of cement slurry without compromising its integrity and performance.

It is another object of this invention to determine multiple cement properties in one system which requires substantially less maintenance work than other designs yet meet industry standards of accuracy, repeatability, durability, and ease of cleaning.

SUMMARY OF THE PRESENT INVENTION

The present invention pertains to a method and experimental apparatus for studying properties of cement slurry to be used in oil or gas well under varied pressure and temperature conditions. This apparatus can be used to predict the likelihood of gas migration, compressive strength and static gel strength of cement. It comprises a servo motor and coupling magnets to drive a paddle at a very slow speed through the cement in a pressure vessel, a pair of acoustic transducers to generate an acoustic signal and record the transit time of the acoustic signal after it transits the cement, and a gas injection system to evaluate the potential and severity of gas migration of cement sample.

DRAWING FIGURES

Other objects, features and advantages will be apparent from the following detailed descriptions of embodiment taken in conjunction with accompanying drawing in which.

REFERENCE NUMERALS IN DRAWINGS

Figure 1:
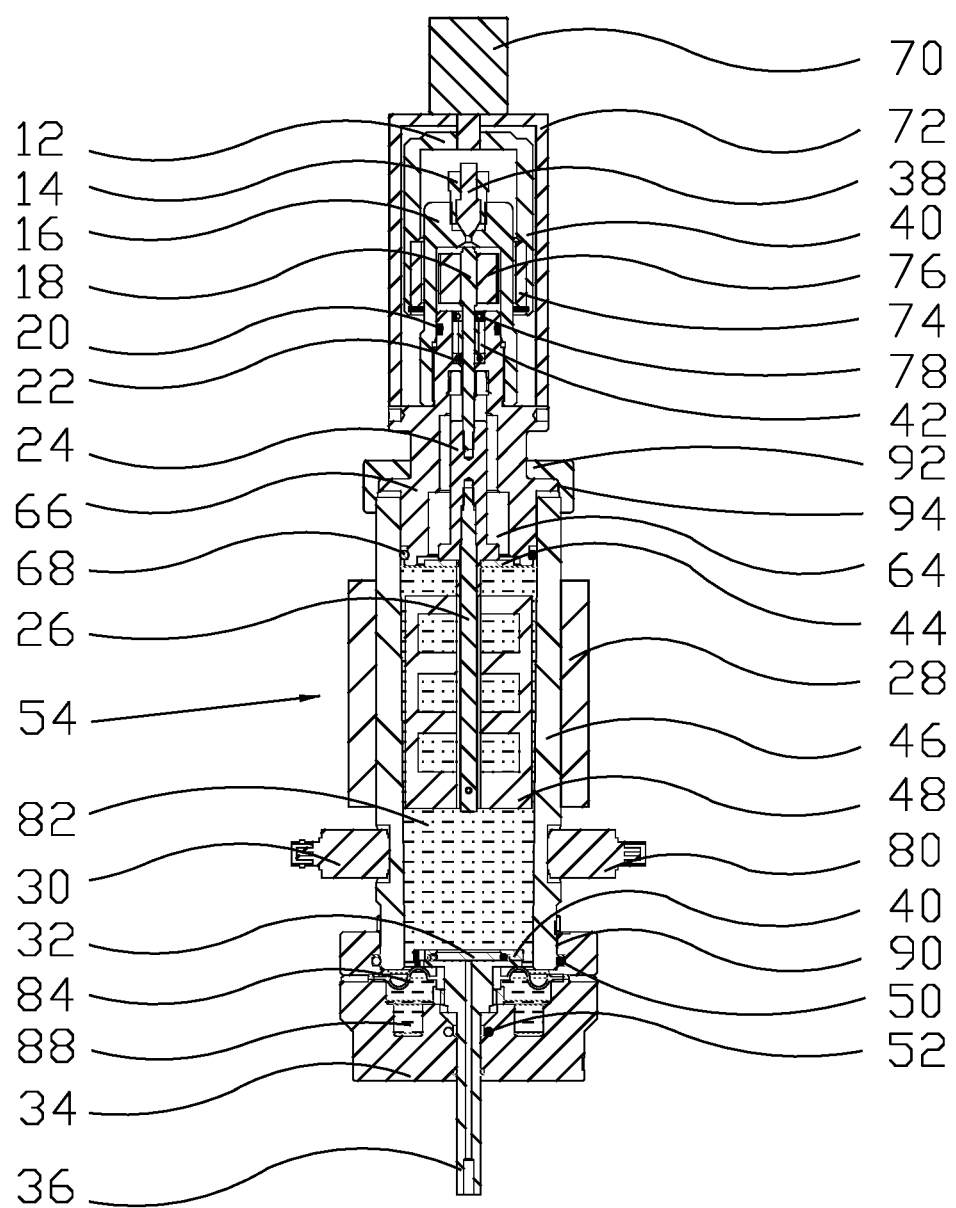
FIG. 1 is a cross sectional view of cement analyzer cell assembly.

| | |
|---|---|
| 12 Magnet mount | 14 Plug |
| 16 Magnet cap | 18 Shaft |
| 20 O-ring | 22 Bearing |
| 24 Coupling | 26 Shaft |
| 28 Heater | 30 Ultrasonic transducer |
| 32 Filter disc | 34 Retainer |
| 36 Stem | 38 Gland plug |
| 40 Stem cover | 42 Spacer |
| 44 Diaphragm | 46 Pressure vessel |
| 48 Paddle | 50 O-ring |
| 52 O-ring | 54 Cement analyzer cell assembly |
| 56 Volumetric flask | 58 Accumulator |
| 60 Back pressure system | 62 Flow controller and meter |
| 64 Reduced opening | 66 Vessel cap |
| 68 O-ring | 70 Motor |
| 72 Motor support | 74 Outer magnet |
| 76 Inner magnet | 78 Bearing |
| 80 Ultrasonic transducer | 82 Cement sample |

| REFERENCE NUMERALS IN DRAWINGS | |
|---|---|
| 84 Diaphragm | 86 Pressure measurement device |
| 88 Pressure media | 90 Thread |
| 92 Cap retainer | 94 Thread |

Description—FIG. 1—Preferred Embodiment

Embodiments disclosed herein relate to an apparatus that measures multiple cement properties, such as severity of gas migration, static gel strength and compressive strength under varied pressure and temperature conditions.

FIG. 1 is a cross-section view of a cement analyzer cell assembly 54 that consists of a cylindrical pressure vessel 46 and a retainer 34. Retainer 34 is detachable from pressure vessel 46 through a thread 90. An o-ring 50 assures against fluid leakage from the junction of pressure vessel 46 and retainer 34. A stem 36 is inserted into pressure vessel 46 for gas injection from cell bottom in order to measure severity of gas migration of a cement sample 82. An o-ring 52 assures against fluid leakage from the junction of retainer 34 and stem 36. A filter disc 32 is attached to stem 36 and is secured by a stem cover 40. A diaphragm 84 is attached to stem 36 for separating a pressure media 88 from cement sample 82 when diaphragm 84 is pushing against cement sample 82 for simulating confining pressure. Inside of pressure vessel 46, a paddle 48 is attached to a shaft 26. A reduced opening 64 is positioned between top section and lower section of pressure vessel 46. A diaphragm 44 is attached to shaft 26 disposed at reduced opening 64 for containing cement sample 82 agitation below itself. A vessel cap 66 rests on pressure vessel 46 and is secured by a cap retainer 92 via a thread 94. An o-ring 68 assures against fluid leakage from the gap between inside wall of pressure vessel 46 and outside wall of vessel cap 66.

A motor 70 is mounted on a motor support 72 that rests on the top of vessel cap 66. A magnet mount 12 is rotationally supported on the inside wall of motor support 72. An outer magnet 74 is mounted on magnet mount 12 at a considerably same level where coupling an inner magnet 76, which is attached to a shaft 18 inside of a magnet cap 16. Magnet cap 16 is detachable from vessel cap 66 that is sealed by an o-ring 20. A gland plug 38 and a plug 14 are inserted on the top of magnet cap 16 to prevent fluid from leaking. Shaft 18 passes through the center of vessel cap 66 and is rotationally supported by a bearing 22, a spacer 42 and a bearing 78. Shaft 18 is connected to shaft 26 through a coupling 24. Motor 70 drives paddle 48 to rotate through shaft 18 and shaft 26. A heater 28 is used to reach and maintain desired testing temperature. An ultrasonic transducer 30 and an ultrasonic transducer 80 are installed on the side wall of pressure vessel 46 for determining compressive strength of cement sample 82. Ultrasonic transducer 30 generates an acoustic signal which is transmitted through cement sample 82. Ultrasonic transducer 80 measures and records the transit time of the acoustic signal after it transmits cement sample 82. This data is processed and compressive strength is determined based on relationship between the transit time of ultrasonic signal and compressive strength by a computer processor, or anything equivalent with data processing capability.

Operation—FIG. 1—Preferred Embodiment

Begin assembly of cement analyzer cell assembly 54 by installing outer magnet 74 on the inner wall of magnet mount 12. Assemble motor support 72 and magnet mount 12 together. Attach inner magnet 76 to shaft 18. Install bearing 22, spacer 42 and bearing 78 into vessel cap 66, then vertically insert shaft 18 into vessel cap 66 through bearing 22, spacer 42 and bearing 78. Next, insert o-ring 20 and screw magnet cap 16 onto vessel cap 66. Insert gland plug 38 and plug 14 into magnet cap 16. Install diaphragm 44 and attach paddle 48 to shaft 26. Connect shaft 26 to shaft 18 via coupling 24.

Install o-ring 52, o-ring 50 and diaphragm 84 onto retainer 34. Then install filter disc 32 onto stem 36 by screwing stem cover 40 onto filter disc 32. Next vertically insert filter disc 32 with stem 36 into retainer 34 through the center hole of diaphragm 84. Attach retainer 34 to pressure vessel 46. Pour cement sample 82 into pressure vessel 46. Install o-ring 68 onto vessel cap 66, then put vessel cap 66 to rest on pressure vessel 46. Place cap retainer 92 over vessel cap 66 and screw it via thread 94. Install motor 70 on motor support 72 and attach magnet mount 12 to the shaft of motor 70. Then install ultrasonic transducer 30 and ultrasonic transducer 80 onto pressure vessel 46.

Due to the magnetic coupling between outer magnet 74 and inner magnet 76, shaft 18 rotates at the same revolving speed as magnet mount 12 does. Because of the consistency of cement sample 82, a torque is required to rotate paddle 48. This toque is originated from motor 70, and operator can retrieve the measurement of static gel strength from this torque generated by motor 70 to initiate the movement of cement sample 82.

Figure 2:
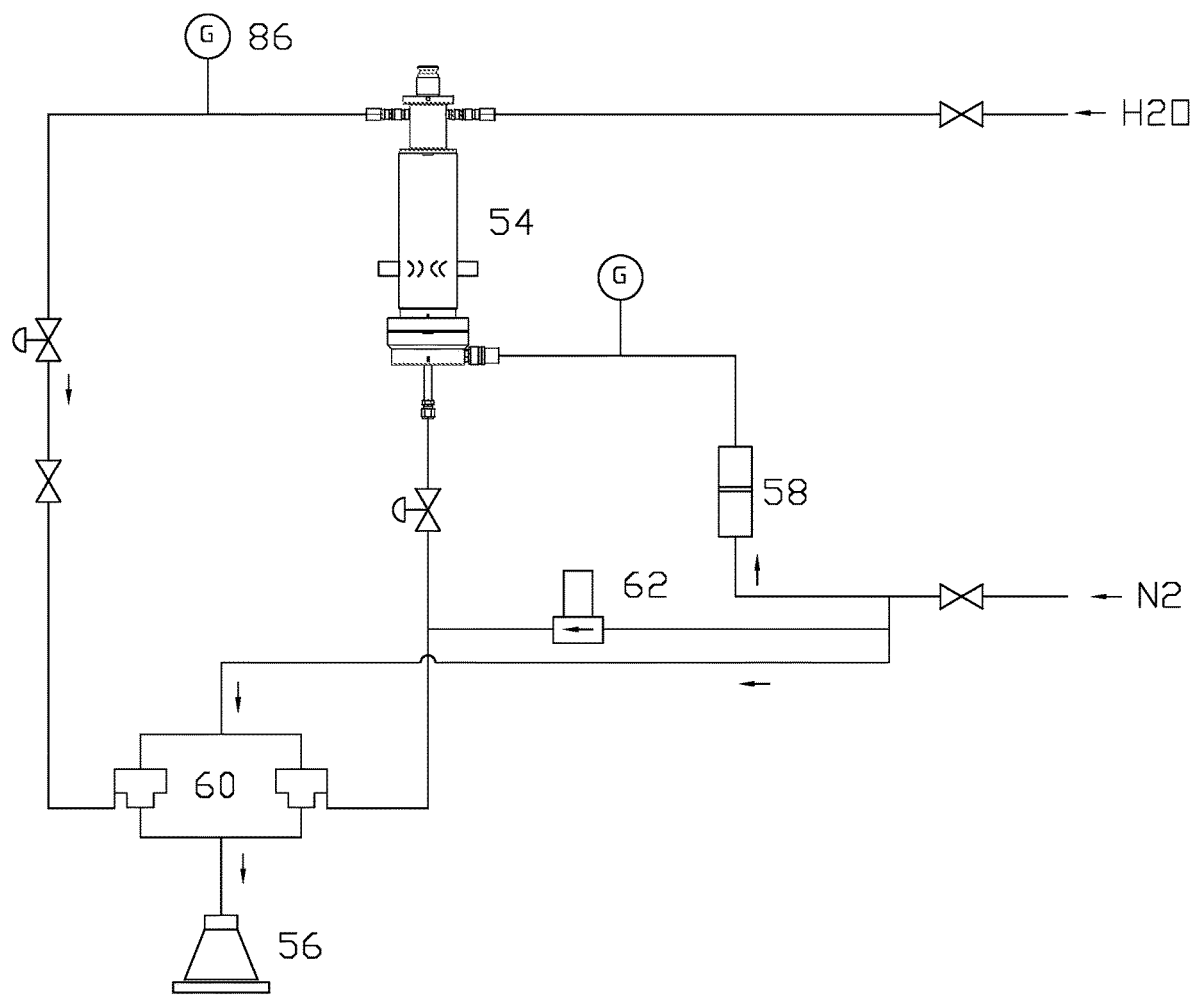
FIG. 2 is a flow diagram of cement analyzer system.

Description—FIG. 2—Preferred Embodiment

FIG. 2 shows a schematic flow diagram of cement analyzer system. In order to apply confining pressure on cement sample 82, cement analyzer cell assembly 54 is connected to an accumulator 58. Accumulator 58 will inject pressure media 88 into cement analyzer cell assembly 54 to push diaphragm 84 against cement sample 82.

A gas flow controller and meter 62 connected to cement analyzer cell assembly 54 is used to control flow rate of gas migrating. Said gas flow controller and meter 62 can be a Digital Mass Flow Controller and Mass Flow Meter, or equivalent, such as Sierra Premium Digital Mass Flow Controllers and Mass Flow Meters SmartTrak®100. The severity of gas migration will be determined based on the pressure difference between gas injecting pressure and outlet pressure read by a pressure measurement device 86. A back pressure system 60 and a volumetric flask 56 are used to provide back pressure and receive filtrate.

Operation—FIG. 2—Preferred Embodiment

Connect the tubing lines as shown in FIG. 2. First, purge and fill all tubing lines with water including accumulator 58. Nitrogen supply will push a pressure medium inside accumulator 58 for generating confining pressure on cement sample 82 inside cement analyzer cell assembly 54. Back pressure system 60 is used to provide desired back pressure.

Volumetric flask 56 collects the filtrate when filtrate pressure is above back pressure, which is also the bottom pressure of cement analyzer cell assembly 54. Back pressure is controlled and maintained by Back pressure system 60. Flow controller and meter 62 controls flow rate of nitrogen, and pressure measurement device 86 reads the pressure at the top of cement analyzer cell assembly 54. The pressure difference between the top of cement analyzer cell assembly 54 and the bottom of cement analyzer cell assembly 54 at which pressure is controlled and maintained by 60 Back pressure system, combining with nitrogen flow rate of meter 62, can be used to determine severity of gas migration.

CONCLUSION, RAMIFICATIONS, AND SCOPE

Accordingly, the reader will see a cement analyzer cell assembly 54 used to determine static gel strength, compressive strength and severity of gas migration of cement sample 82 at different conditions.

A ramification of the preferred embodiment is that paddle 48 does not have to be driven with a magnet coupling across magnet cap 16. Paddle 48 could be driven to rotate with a means such as directly driven at top of motor support 72 with dynamic seal, etc.

A ramification of the preferred embodiment is that gas inlet or gas outlet could locate at the side wall of pressure vessel 46, instead of at ends of cement analyzer cell assembly 54.

A ramification of the preferred embodiment is that confining pressure could be applied through other methods and means, such as directly applying confining pressure from the top of cement analyzer cell assembly 54 through a fluid, instead of through diaphragm 84 at bottom.

A ramification of the preferred embodiment is that instead of measuring pressure difference when gas migrate within cement sample 82, operator could keep inlet and outlet gas pressure constant, while measuring gas flow rate by using flow controller and meter 62.

A ramification of the preferred embodiment is that pressure media 88 could be gas, liquid, etc.

It will be apparent to those skilled in the art that other embodiments, improvements, details, and uses can be made consistent with letter and spirit of the foregoing disclosure and within the scope of this patent, which is limited only by the following claims, construed in accordance with the patent law, including, the doctrine of equivalents.

Objects and Advantages

From the description above, a number of advantages of present invention become evident:

a. Very economically measuring static gel strength, compressive strength and severity of gas migration of cement sample in one unit.
b. Due to the limited number of components and configuration, the current invention is easy to manufacture, operate and requires low maintenance.

Further objects and advantages of my invention will become apparent from a consideration of the drawings and ensuing descriptions.

The invention claimed is:

1. A cement analyzer instrument is used to determine gas migration and compressive strength, including:
    a) a pressure vessel filled with a sample fluid,
    b) a gas inlet to provide gas injection,
    c) a means to measure a pressure difference of said sample fluid when said gas migrates through said sample fluid,
    d) a pair of ultrasonic transducers to generate and record an acoustic signal transmitted through said sample fluid, and
    e) a means to measure a transit time of said acoustic signal through said sample fluid.

2. The instrument of claim 1 further comprising a means to apply a confining pressure on said sample fluid by a pressure media.

3. The instrument of claim 2 further comprising a diaphragm for separating said sample fluid from said pressure media.

4. The instrument of claim 1 further comprising a flow controller and meter for controlling said gas migrating.

5. The instrument of claim 1 further comprising a means to measure a filtrate of said sample fluid.

6. The instrument of claim 1 further comprising a heater to reach and maintain desired test temperature.

* * * * *